United States Patent [19]

Ayer

[11] Patent Number: 5,293,219
[45] Date of Patent: Mar. 8, 1994

[54] FIBER LENGTH ANALYZER

[75] Inventor: John A. Ayer, Lynnfield, Mass.

[73] Assignee: Andritz Sprout-Bauer, Inc., Muncy, Pa.

[21] Appl. No.: 815,258

[22] Filed: Dec. 31, 1991

[51] Int. Cl.$^5$ ................. G01B 11/02; G01N 15/02
[52] U.S. Cl. ........................ 356/383; 356/335; 356/440
[58] Field of Search ................. 356/383–385, 356/244, 246, 335–343, 39, 73, 410, 440–442; 250/458.1, 461.2

[56] References Cited

U.S. PATENT DOCUMENTS

| | | |
|---|---|---|
| 3,461,030 | 8/1967 | Keyes . |
| 3,498,719 | 3/1970 | Wing et al. . |
| 3,518,003 | 6/1970 | Meyn . |
| 3,652,850 | 3/1972 | Briggs . |
| 3,724,957 | 4/1973 | Tamate et al. . |
| 3,739,183 | 6/1973 | Burton et al. . |
| 3,818,200 | 6/1974 | Pilhofer ............... 356/335 |
| 3,823,320 | 7/1974 | Ledoux . |
| 3,879,129 | 4/1975 | Inoue . |
| 3,980,517 | 9/1976 | MacTaggart . |
| 4,066,492 | 1/1978 | Hill . |
| 4,110,043 | 8/1978 | Eisert ................. 356/102 |
| 4,225,385 | 9/1980 | Hughes, Jr. et al. . |
| 4,266,874 | 5/1981 | Janin et al. .......... 356/335 |
| 4,318,180 | 3/1982 | Lundquist et al. . |
| 4,352,558 | 10/1982 | Eisert ................. 356/336 |
| 4,477,187 | 10/1984 | Pettit et al. .......... 356/335 |
| 4,554,051 | 6/1985 | Danforth . |
| 4,596,036 | 6/1986 | Norgren et al. ........ 356/336 |
| 4,606,631 | 8/1986 | Anno et al. ........... 356/338 |
| 4,660,152 | 4/1987 | Downing et al. ....... 356/442 |
| 4,692,210 | 9/1987 | Forrester . |
| 4,758,308 | 7/1988 | Carr . |
| 4,837,446 | 6/1989 | Renard et al. ......... 250/461.1 |
| 4,895,019 | 1/1990 | Lehmikangas et al. . |
| 4,933,291 | 6/1990 | Daiss et al. ........... 356/244 |
| 4,966,462 | 10/1990 | Novick ............... 356/442 |

FOREIGN PATENT DOCUMENTS

| | | |
|---|---|---|
| 2621217 | 12/1976 | Fed. Rep. of Germany . |
| 2512196 | 3/1983 | France . |
| WO91/14169 | 9/1991 | PCT Int'l Appl. . |
| 1164719 | 9/1969 | United Kingdom . |

OTHER PUBLICATIONS

Advances in Testing Oct. 1988 Tappi Journal pp. 19, 215.
Acousto–Optical Fiber Characterization Aug. 1989 Tappi Journal pp. 171–173.
Laser Technology Offers New Way to Measure Furnish Components Pulp & Paper Canada 89:9 (1988) pp. 25–27, 29, 31, 32.
T 233 SU-64 Method—1953 Revised—1964 Fiber Length of Pulp by Classification Tappi Standard.
An Evaluation of the Comparative Performance of the Kajaani FS-100 and FS-200 Fiber Length Analyzers Dec. 1988 Tappi Journal pp. 149–155.
Brochure—Shive Analyzer Pulmac Montpelier, Vermont.
Brochure—The Kajanni FS-200.
Utilization of Drainage and Fiber Length Measurements in TMP Plant Matti Luvkkonen Taina Sopenlehto Hannu Suutari Kajaani Electronics Ltd. 1989 Annual Meeting.

Primary Examiner—Richard A. Rosenberger
Assistant Examiner—Hoa Q. Pham
Attorney, Agent, or Firm—Chilton, Alix & Van Kirk

[57] ABSTRACT

A measuring cell (22) in a fiber sample analysis system (10) contains housing member (76) which removably supports a transparent flow tube (82) and an optical device (26) which projects a beam (124) across the tube for detecting and measuring individual fibers in a dilute sample fluid which flows through the tube at a constant velocity. The tube includes a gradually narrowing transition portion (86) leading to a measurement portion (88) situated at the optical device and having a flow diameter in the range of about 1.0 to 3.0 mm.

24 Claims, 9 Drawing Sheets

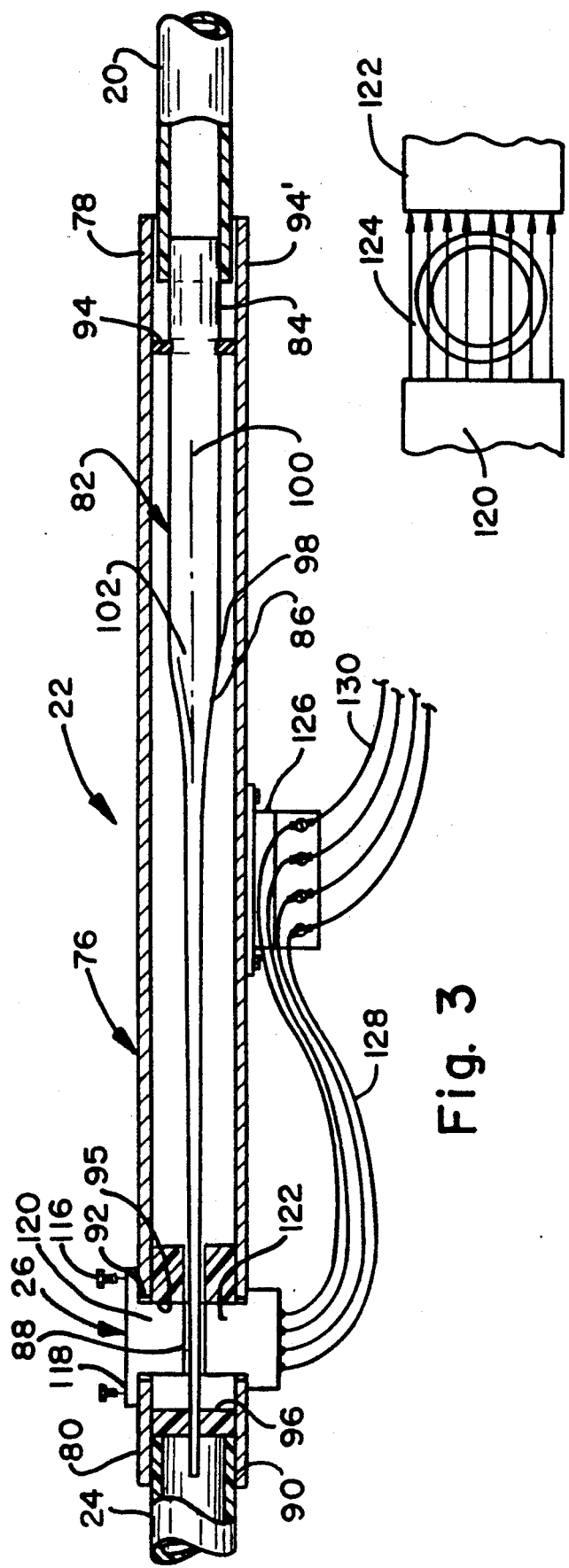
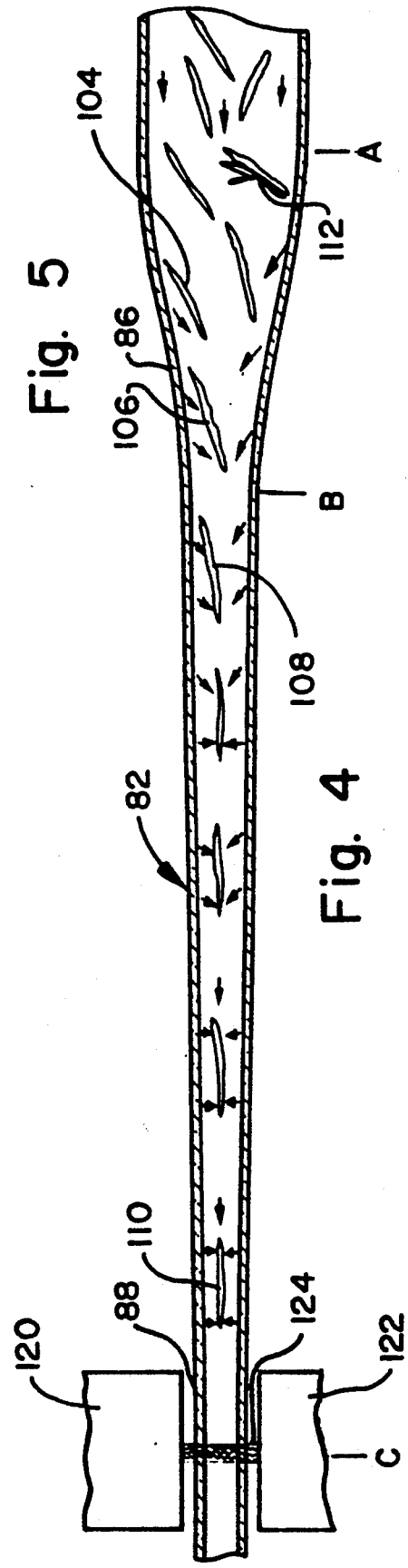
Fig. 3
Fig. 4
Fig. 5

FIBER LENGTH ANALYZER

BACKGROUND OF THE INVENTION

The present invention relates to the detection of particulates in a fluid, and more particularly, to the measurement of the size distribution of fibers in a fluid sample.

In papermaking and other processes of a similar nature, a dispersion of fibers in a carrier liquid is deposited on webs or the like for undergoing various consolidation, drying, and perhaps coating operations, eventually to emerge as a finished sheet product, i.e., paper. The manufacture of paper spans a variety of specifications as to weight, surface texture, and other physical and chemical criteria to be satisfied. As is well known, the quality of the manufactured paper is very strongly dependent on the quality of the fibers. This quality depends in part on the source of the fibers, and on the manner in which the fibers were refined prior to introduction into the paper manufacturing equipment. An indicator of refining quality is the size distribution of the refined fibers.

In papermaking plants, it is desired that the machinery be adjusted, or controlled, in response to the deviation of the fiber size distribution relative to the targets associated with the particular type of paper manufactured during a given run. To date, on-line equipment for measuring or analyzing the size distribution of fibers, has been very expensive and susceptible to plugging.

Traditionally, "accurate" fiber size distribution has been determined by flowing a diluted sample through various tanks and meshes, on which the fibers are physically classified into four or five size intervals. The deposits on each mesh must be dried and weighed. As a practical matter, this procedure cannot be carried out on line, because the steps of precisely diluting the samples, weighing the meshes before and after classification, and the like, can only be performed in a laboratory or a well-equipped room away from the actual paper manufacturing equipment. The standard types of procedures are generally referred to as either the Clark method or the Bauer-McNett method, and are more fully described in TAPPI Standard T233SU-64 (1964).

More recent attempts of on-line measurement have utilized an optic counting technique, whereby a diluted sample of the fluid is passed through a transparent tube, where a standing light beam is interrupted commensurate with the length of the fiber passing therethrough. It is believed that one type of optic analyzer, available in two models, utilizes measuring tubes having diameters of about 0.2 mm and 0.4 mm, and counting rates of 50 and 100 fibers per second, respectively. Since relatively large fibers, or the occasional agglomeration of fibers, better known as shives, may have a diameter on the order of 0.2 mm to 0.4 mm, this type of equipment is prone to plugging by oversize fibers or shives. When plugging occurs, a backwash or vacuum assist operation is performed to clear the tubes and resume analysis.

Another type of optic analyzer has a generally square flow tube on the order of at least 8.0 mm per side. In this arrangement, the flow area is large enough to avoid blockage by oversized fibers and shives, but it is so large that two light beams projecting perpendicularly to each other, must be used to assure that the fibers can be characterized. Precision is lost and, as a result, the fibers are classified only into only a few categories, e.g., relatively large, average, or relatively small.

SUMMARY OF THE INVENTION

It is an object of the present invention to provide an optic fiber size analyzer which may be used on line, is less susceptible to plugging, and can accurately discriminate slight size variations from fiber to fiber.

It is a further object of the invention, that the fiber analyzer exhibit very high sensitivity to the presence of particulates in an otherwise relatively pure liquid medium, whereby such particulates may be discriminated and counted at very low concentrations.

It is yet another object of the invention to provide an optic-based fiber length analyzer in which a measurement cell containing a transparent flow tube and an optic measuring device, can be replaced easily.

These and other objects and advantages of the invention are provided in accordance with the invention, by a system in which a flow of diluted sample fluid is directed through a rigid tube which tapers gradually with a flow area reduction of at least about 75% to a substantially cylindrical, transparent, measurement portion across which a single light beam is projected for measuring each of the fibers as it intercepts the beam. By gradually reducing the flow cross-section into an elongated, cylindrical, measurement portion, the tube has the effect of directing the fibers gradually toward the longitudinal axis of the tube. As the fibers move toward the axis, they accelerate to a known velocity and inherently settle on a flow path that produces equal pressure on all lateral surfaces of the fiber. This pressure equalization occurs substantially only on the axis of the tube, by analogy to the pressure distribution within a pipe having laminar, i.e., non-turbulent flow.

The flow tube measurement portion has a flow diameter of between about 1 and 3 mm, preferably 1.5 to 2.5 mm, and accommodates a flow velocity in the range of about 150–200 feet per second. It is believed that the high flow friction at the walls of the narrowing tube in comparison with the lower flow resistance at the axis of the tube, tends to orient each fiber axially and maintain it on the axis, i.e., off the tube wall. It is believed that this phenomena begins to occur in the conical, or transition portion of the tube, such that the fiber has nearly oriented itself on the axis as it enters the measurement portion of the tube, where it remains centered. Even the larger fibers and shives which may enter the narrow, measurement portion of the tube, tend not to hang up and accumulate to plug the tube.

Since the fibers tend to pass serially through the measurement tube on the axis, each fiber intercepts the light beam at substantially the identical position in the beam. This consistency in the measurement position, contributes to the sensitivity to fiber size variations. For example, in the preferred embodiment having a tube measurement portion diameter of about 1.5 mm, 256 length intervals are easily discriminated within the range of fiber length from about 0.0–7.20 mm and width up to about 1.0 mm. High sensitivity is also achieved by the use of a slotted optical switch which projects an infrared ribbon beam from a gallium-arsinide LED, and generates an analog output signal from which indications of both fiber length and width are sensed.

In the preferred embodiment, the optical device and an elongated, tapered, glass flow tube are supported in a housing or holder, which itself is substantially tubular. Generally annular support and/or sealing structure are provided in the housing interior near the narrow, measurement portion of the tube, adjacent the optical device, which is rigidly attached to the housing. The internal support member, preferably near the outlet end of the housing, defines a small receiving aperture on the axis. In this manner, the small-diameter measurement portion of the tube, which is more fragile, can easily pass through the inlet end of the housing and continue moving substantially centrally in the housing so as to pass through the support member adjacent the optic device as the larger, trailing portion of the tube fully enters the housing. Thus, the tube can be readily replaced without removing the housing from its support within the analyzer package and without detaching the optic device from the housing. The measurement cell including tube, housing, and optical device can also be easily replaced as a unit.

The analyzer package is preferably arranged such that the measurement cell is secured to a hinged wall or door of the package. When the tube or cell requires replacement, the door can be swung open to expose the cell. The inlet and outlet conduits to the cell can easily be detached, and the cell or tube replaced.

BRIEF DESCRIPTION OF THE DRAWINGS

FIG. 3 is a longitudinal section view of the measuring cell of the system shown in FIG. 1;

FIG. 4 is an enlarged schematic view of the measurement portion of the flow tube that is intercepted by the light beam, showing how the fibers align themselves for serial passage through the light beam;

FIG. 5 is a view along the axis of the measuring tube, showing the light beam;

DESCRIPTION OF THE PREFERRED EMBODIMENT

Figure 1:
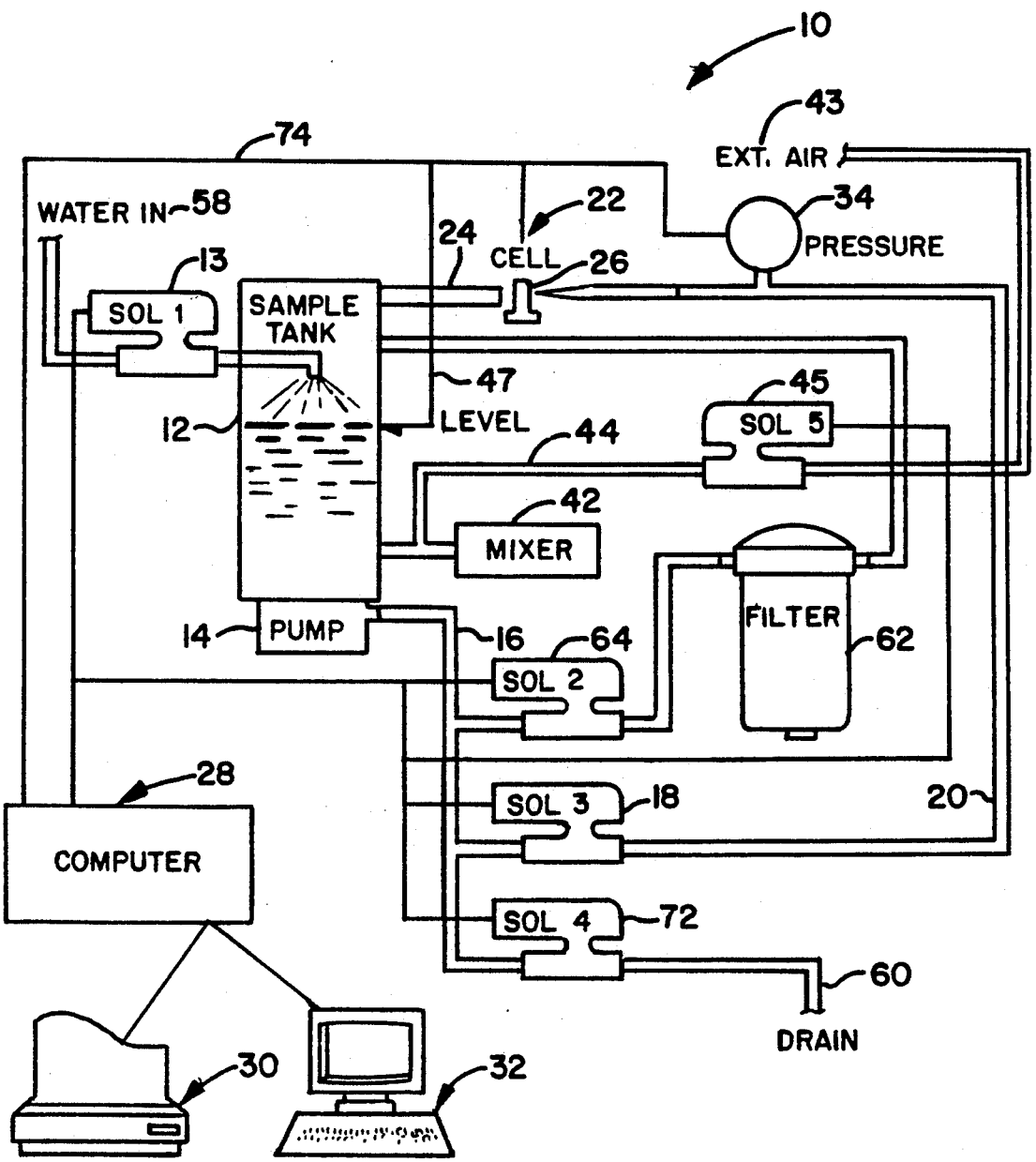
FIG. 1 is a schematic view of one embodiment of the invention, for analyzing the fiber size distribution of a sample deposited in a sample tank.

FIG. 1 shows the main components of one embodiment of the fiber analyzer system 10 in accordance with the present invention. The fibers are introduced into a sample tank 12 where agitation or other means are preferably provided, such as bubbling or mixing, to maintain the fibers in a suspended, or dispersed condition in the liquid, typically water. The concentration of fibers in the sample tank 12 should preferably less than about 0.001%. A pump 14 or other means for drawing the fluid from the tank, without cutting the fibers, is provided to generate a substantially constant volumetric flow rate through line 16 to solenoid 18 and then into a first conduit or cell inlet line 20. This conduit 20 is connected to a measurement cell shown generally at 22, where individual fibers pass through a beam of light and are sensed as to length and, preferably, width, in a manner to be described in greater detail below.

In the embodiment of FIG. 1, the fluid discharged from the cell outlet into a second conduit 24, is returned to the sample tank 12 but in another embodiment the discharge flow can be discarded. A valve 34 or other automatic or manually operated device and associated pressure are preferably provided in the first conduit 20 immediately upstream of the measuring cell 22, to produce a constant, and preferably predetermined, flow velocity through the cell.

The optical detector 26 at the cell 22, is preferably connected to a special purpose digital computer or programmable logic device 28 and/or a personal computer 32, where data are gathered, reduced, and recorded or printed 30, and where the operator can control various functions in the process. These functions will now be further described with reference to FIGS. 1, 2 and 7.

Figure 2A:
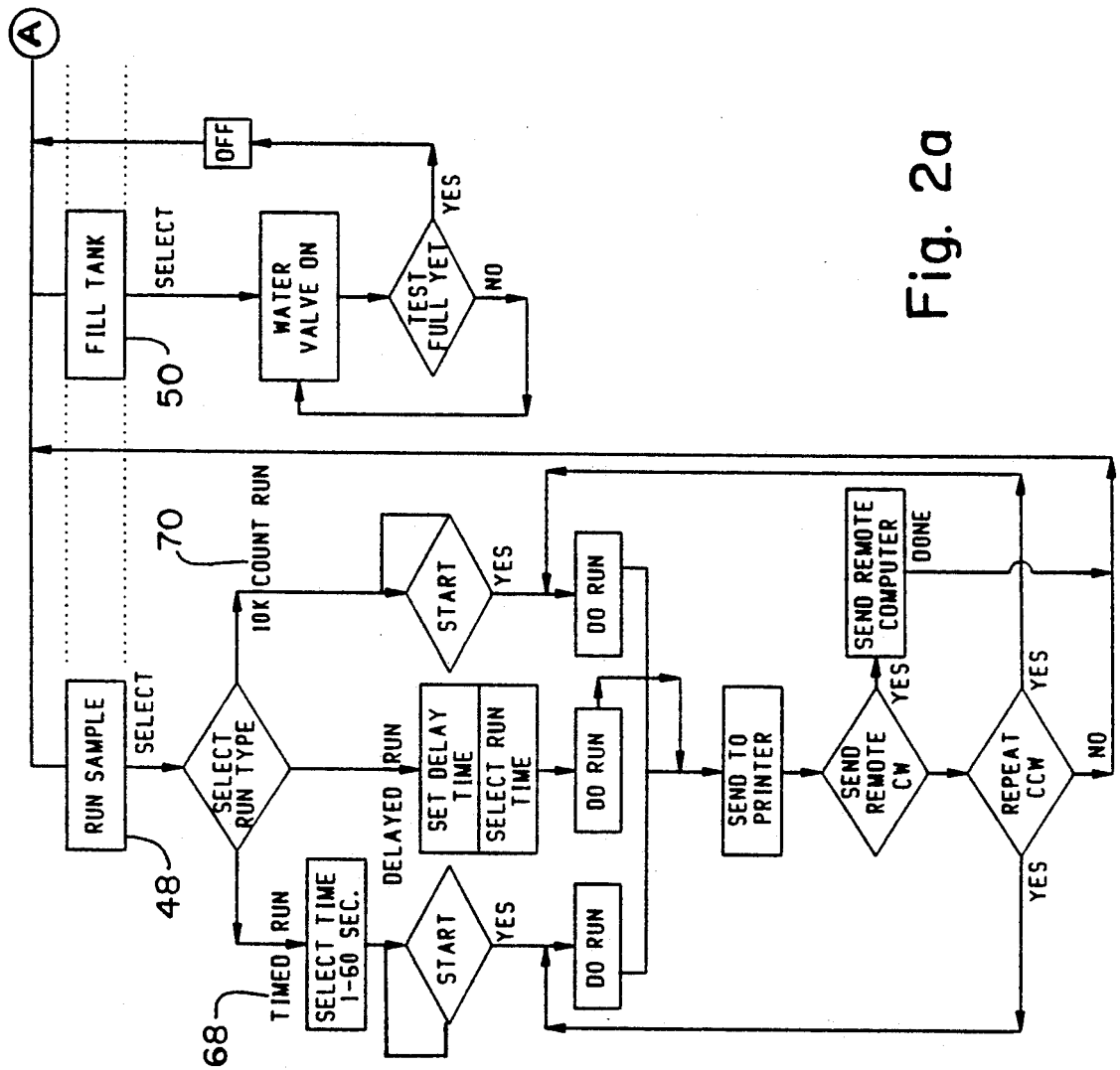
FIGS. 2a, 2b are a flow diagram showing the preferred functional capabilities of the system shown in FIG. 1.
Figure 2B:
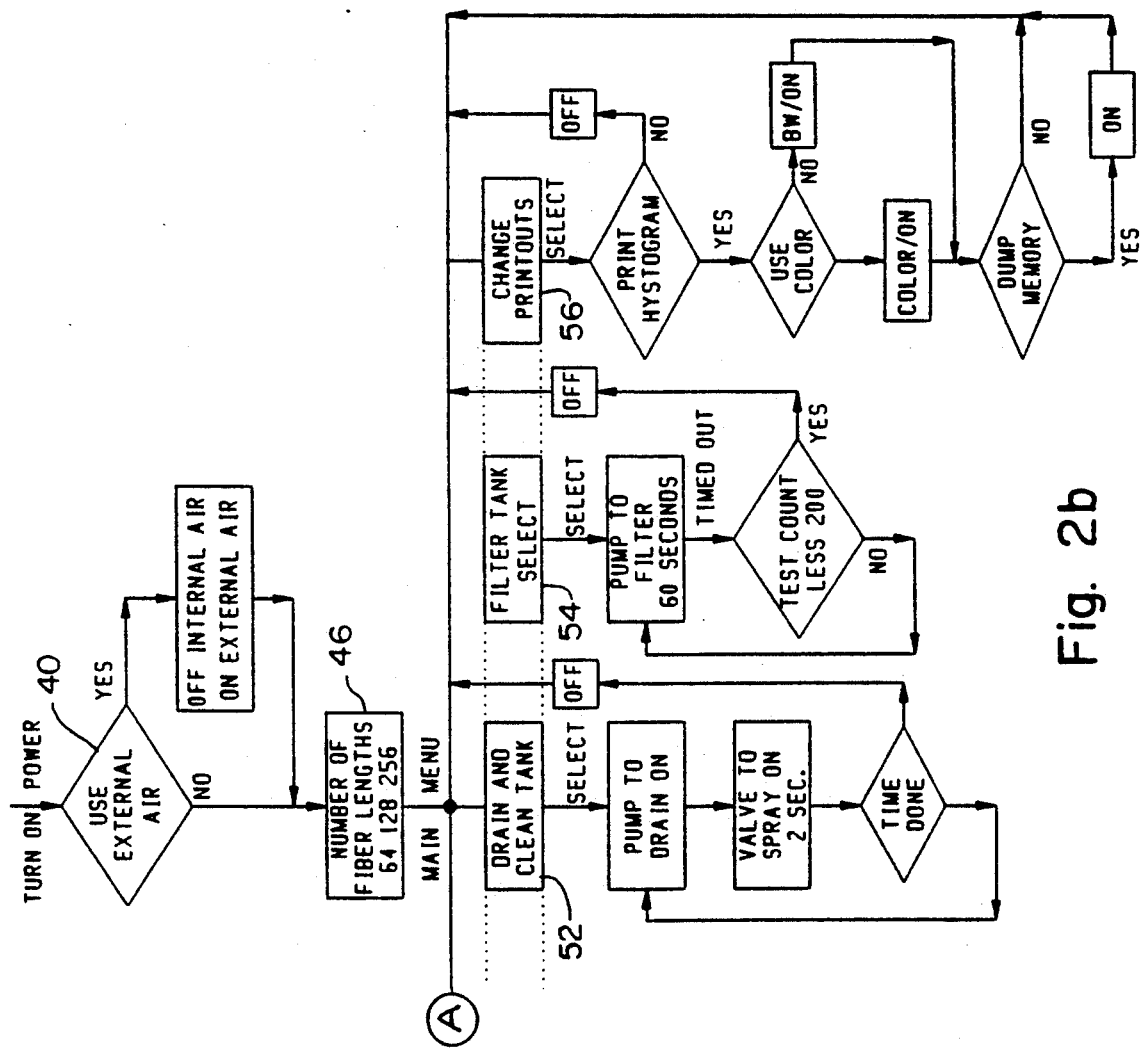
Figure 7:
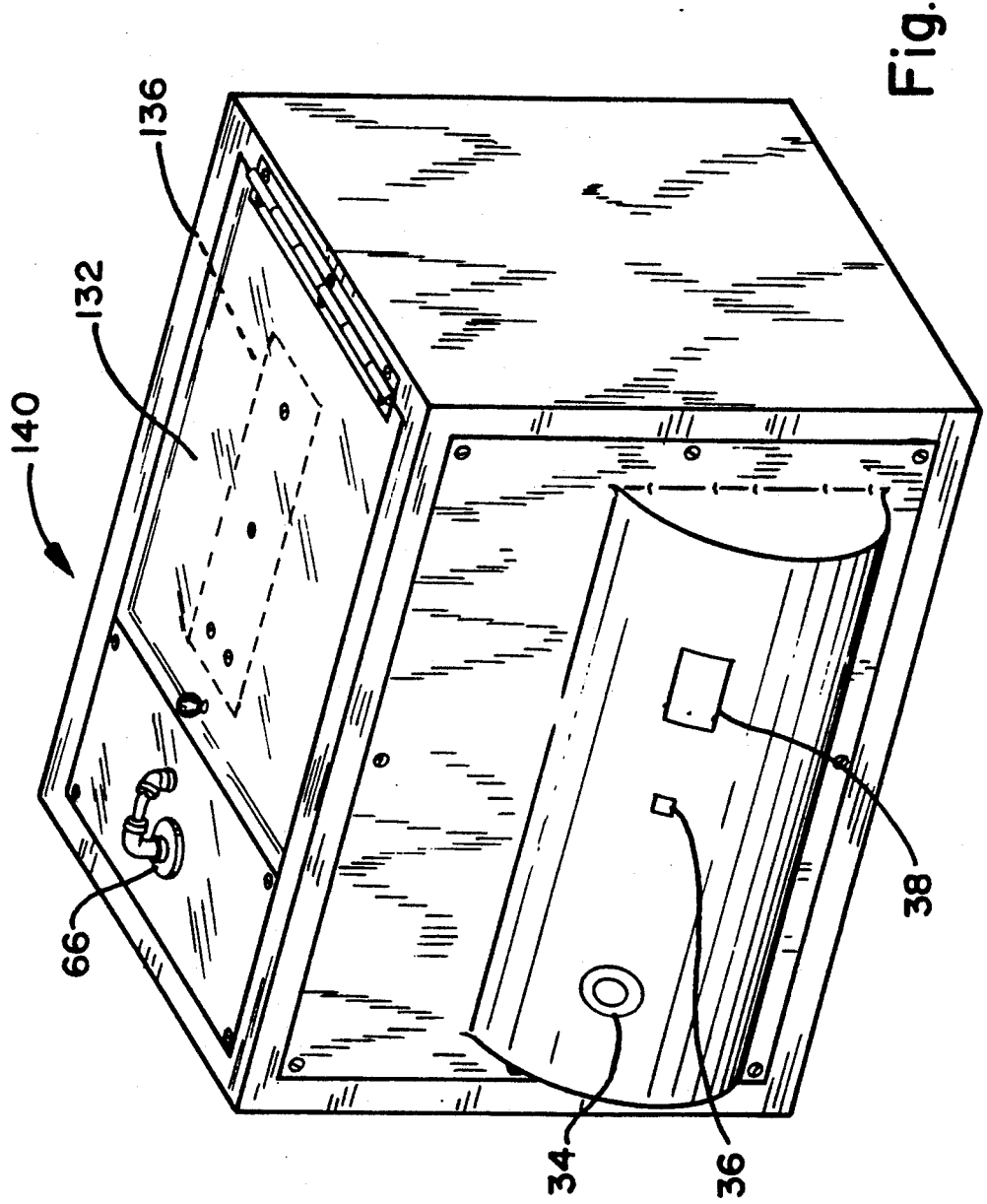
FIG. 7 is a perspective view of the preferred packaging of the analyzer of FIG. 1.

The computer 28 can be under the control of a straightforward program having the menu and function architecture shown in FIG. 2, via a simplified interface shown in FIG. 7. The analyzer 10 is configured by selecting variables and functions from a simple menu. The operator selects the functions that are to be performed and the type of output that will be sent from the instrument to printer 30 or remote computer 32 once a run has been completed. All user operation can be achieved using the "Select" potentiometer 34 and "Enter" button 36 that are located on the face of the computer box. The operator simply finds the desired function on the menu displayed window 38 using the "Select" potentiometer 34 and then chooses it by pressing the "Enter" button 36. Of course, other interfaces available to one ordinarily skilled in this field can optionally be incorporated into the system 10.

When the power is turned on, the display 38 on the front of the control box will read "USE EXTERNAL AIR" 40. The operator must choose yes or no. If "no" is selected, the instrument will use its own internal compressor 42 to supply the air or other mixing means for agitation of the tank to keep the fibers dispersed. If "yes" is selected, an external source 43 of clean laboratory air can be connected to the air inlet 44 via solenoid 45.

Next, the instrument will ask the operator to choose the number of fiber lengths. The display will read "#FIBER LENGTHS" 46. This will determine the number of classes that the fibers will be put in when they are recorded by the computer. The operator chooses, for example, either 64, 128, or 256 classes. The range of fiber lengths is preferably the same for all three of the classes, e.g. from 0.028 mm to 7.16 mm. However, the steps in length vary proportionally for each class. In the case of 256 classes, the steps are 0.028 mm. The steps for 128 and 64 are 0.056 mm and 0.112 mm, respectively. The device preferably also classes into a plurality, e.g., eight widths of equal intervals ranging from small to large, with the upper limit approximately equal to the tube minimum diameter.

Once these preliminary selections have been made, the instrument will put the operator into the main menu. From this menu, the operator can control all the functions necessary to run the instrument. These are: "RUN SAMPLE" 46, "FILL TANK" 50, "DRAIN and CLEAN TANK" 52, "FILTER TANK" 54, and "CHANGE PRINTOUTS" 56.

Before any runs can be made, the operator first fills the tank 12 with water via solenoid 13. The instrument must be connected to external sources water 58, air 43, and a drain 60. This is to allow the water in the system to be changed between runs to ensure that no fibers remain in the system from one run to another. If the operator selects "FILL TANK" 50, the instrument will fill the tank 12 to the level set by the adjustable level detector 47 on the tank. The operator should set this detector to the height of the desired water level.

Once the sample tank 12 has been filled, the water may need to be run through the filter 62 to eliminate any foreign particles or air bubbles that could give erroneous readings during a run. The user selects "FILTER TANK" 54 to begin the cleaning process. The instrument will pump the water through the filter 62 via solenoid 64 for enough time to eliminate any foreign particles in the water. The amount of filtering needed will depend on the purity of the water used and how clean the tank was after the last run. While cleaning, the instrument will test the water every 60 seconds for 4 seconds until a count below 200 is obtained. This ensures that there will be a minimum of false readings in the run caused by impurities or fines in the water. The filter is good for 2000 gallons of liquid and depending on the purity of the water used, the life of the filter will vary greatly. Pre-filtered water should be used, if available, to extend the life of the filter.

After the water in the system has been purified, the operator adds the sample fibers to the tank, through a hole in the top cover 66 of the tank 12, whereby the fibers drop into the tank. The fiber length analyzer is now ready to make runs with these fibers.

There are two run modes available to the user. These are timed runs and batch runs. To make a run, the operator selects "RUN SAMPLE" 48 from the main menu. The user will now be asked which type of run is to be made.

If a timed test is desired, the operator selects "TIMED RUN" 68 from the "RUN SAMPLE" menu 48. Next, the time of the run must be selected. The display will read "TIME=". The time is selected by the operator by turning the select potentiometer 34 until the desired run time is reached and pushing "Enter" 36 to select this time. The time can be from 1 to 60 seconds. The operator can select "REPEAT RUN", by turning the select potentiometer fully counter clockwise anytime after the run has started but before it ends. The instrument will do a continuous repeat test at the previously selected time interval. This will continue until the select potentiometer is moved away from the fully counter clockwise position. The computer will store in memory all the data for the fibers that pass through the cell over the selected time.

The operator also may select a batch test by selecting "COUNT=10K" 70. This run type will continue to run fibers through the cell until the count reaches ten thousand. The output will consist of the time to reach a count of ten thousand and the length and width for the fibers stored in memory.

If the user wishes to return to the main menu at any time from the run menu, the select potentiometer should be turned fully clockwise. This can only be done when a run is not in progress.

Once the operator has finished making runs with one batch of fibers, the tank must be drained and cleaned. This is to ensure that all the previous fibers are removed from the system. The user selects "DRAIN and CLEAN" 52 from the main menu. The instrument will then drain the system and wait for the operator to select "FILL TANK" 50 again in preparation for another run.

The "CHANGE PRINTOUTS" 56 menu allows the operator to select the amount and format of the output that is sent to the printer. The default setting will send the printer a summary of the run with only basic information included.

Figure 9:
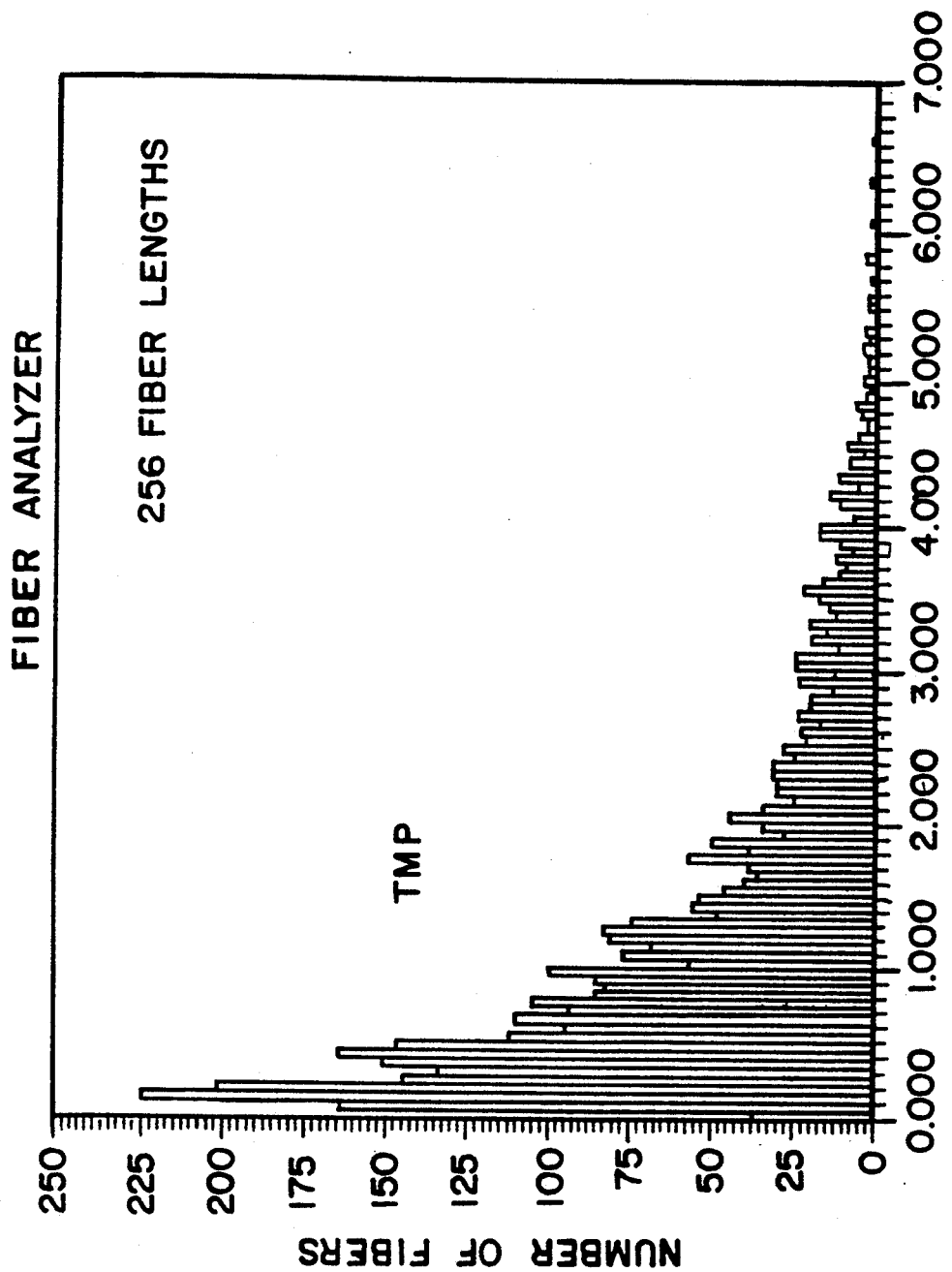
FIG. 9 is one example of the kind of fiber length distribution information that can be obtained from the present invention.

The computer will first ask if the operator wishes to "PRINT HISTOGRAMS". If the operator selects "no", the computer will return to the main menu and no histogram will be printed. If the operator selects "yes", the computer will ask if it should be printed in black and white. The display will read "PRINT B/W". Then, the computer will print out a histogram such as shown in FIG. 9 for the selected number of lengths (64, 128, or 256). A similar histogram can be printed for the width categories. Alternatively, the data can be arranged in matrix format.

Figure 10:
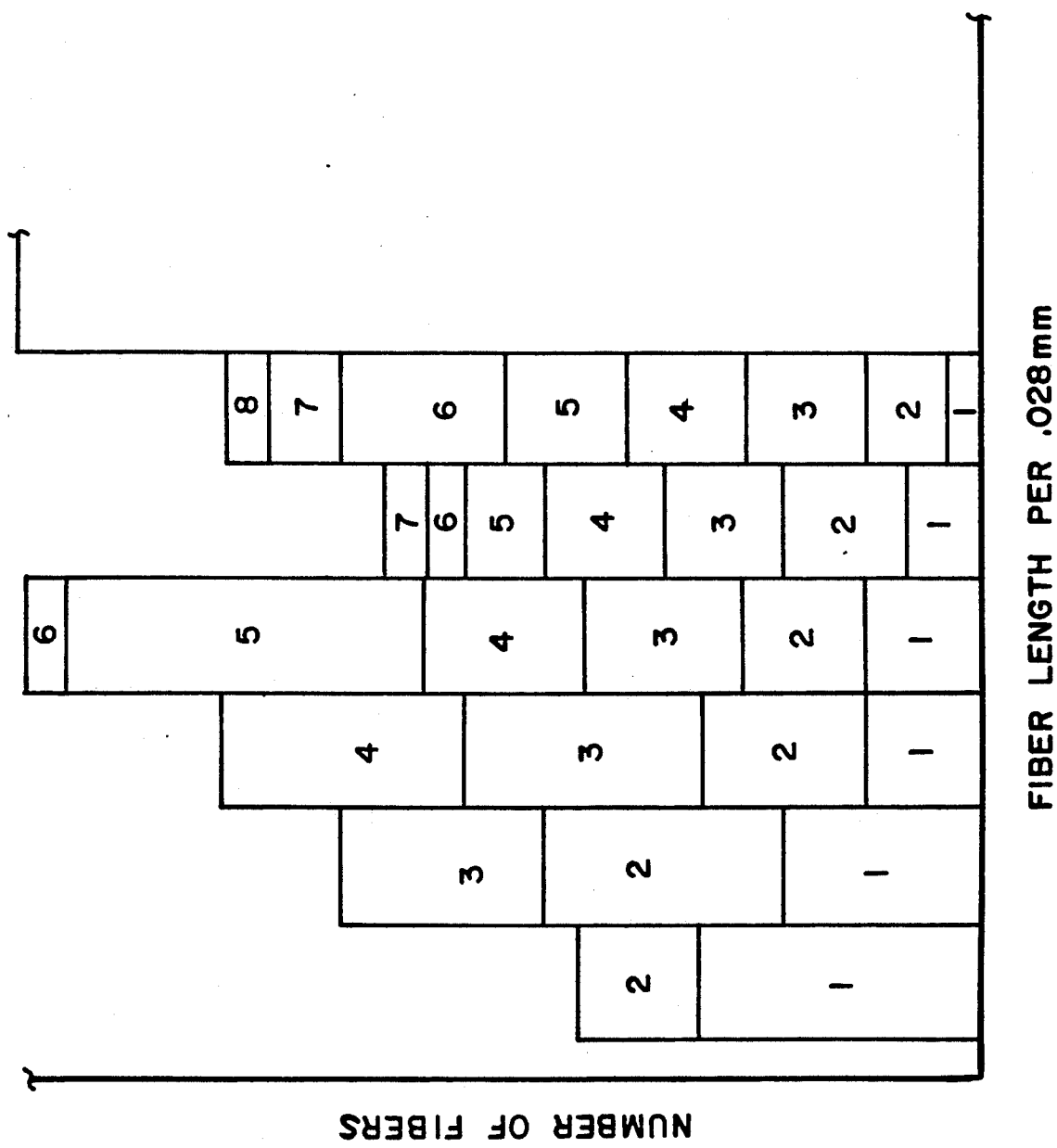
FIG. 10 is another example of fiber length and width distribution information that can be obtained from the present invention.

If the user selects "no", the output will be printed in color form if a color printer is connected. The color histogram output gives the number of fibers in each length category and the different widths that are in each length, represented by different colors in each length. FIG. 10 is an enlarged portion of a "color" histogram, in which eight width categories are schematically represented by the numerals 1–8 instead of colors. The print-out can be set up so that if there is ever a length category where no fibers are found, the relevant matrix entry will show a back-slash.

The basic method of operating the system 10 is to fill the system with water, introduce a batch of fibers into the system, make all desired runs with the fibers, and drain and clean the system via solenoid 72. Alternatively, a sample may be supplied directly to tank 12 from a sample source line (not shown) originating at the refiner and having intermediate dilution.

The fluid pressure in the system is constantly monitored via 74 by the computer 28, and will be displayed and updated on the display for as long as a run is in progress. This is to quickly detect plugging of the cell and to ensure that the velocity of the fibers through the cell is constant during a run. Due to the importance of the predetermined flow rate, the pressure is preferably verified as being within a narrow acceptance range before fiber length data are acquired. The pressure across the cell should preferably remain at about 3 psi for a measurement portion tube diameter of 1.5 mm, producing a preferred flow velocity of about 160 feet per second at the measurement portion. If the pressure goes up drastically during a run, this is an indication that the cell has become plugged with fibers and must be cleaned or replaced before subsequent runs can be made. The pressure in the system is controlled by a small valve 34 located in the line after solenoid 18 and upstream of the cell.

FIGS. 3 and 4 show a preferred form of the measuring cell 22. In general, the substantially tubular, rigid housing 76 has a first or inlet end 78 adjacent the terminus of the first conduit 20, and a second end or outlet 80 adjacent the second conduit 24 or other discharge path. The housing 76 supports and protects an elongated rigid flow tube 82 having a relatively large diameter first end 84, a conical, tapered portion 86, leading into a substantially cylindrical small diameter measurement portion 88 adjacent the second end 90 of the tube. The measurement portion 88, is within a notch or cutout 92 in the housing 76. The housing includes internal structure near the housing ends 78,80, shown for example at 94, 95 and 96 for supporting the tube 82 coaxially within the housing 76.

The tube 82 may have a variety of dimensional relationships for effective operation, but, in general, the flow cross-section at the cylindrical, measurement portion 88 should be no greater than 25%, and preferably between about 10% and 20% of the flow area at the beginning 98 of the tapered portion 86 of the tube. In general, the taper angle 102 relative to the axis 100, should be less than 30°, and preferably less than 15°.

FIG. 4 shows in greater detail, the effect on individual fibers, of the shape of the tube 82. It should be appreciated that, in practice, the individual fibers such as 104,106,108, etc., would be in a more dilute concentration, resulting in somewhat greater separation between fibers, but are shown for illustrative purposes in FIG. 4. For convenience in referring to specific regions of the tube 82, identifying letters A, B and C are provided. At A, which represents the nominal diameter of the tube before tapering, the fibers are distributed in a somewhat random orientation relative to the tube axis. This results from the relatively large diameter, typically at least 8 mm. From regions A to B, the tube wall tapers inwardly to a diameter of less than one-half the diameter at A, with a resulting decrease in flow cross section, by a factor of at least four, i.e., the flow cross section at B is less than 25% of the flow cross section at A.

At C, representing the measurement portion of the tube, the flow diameter is approximately equal to the flow diameter at B. In general, the distance parallel to the axis from B to C, should be long enough for the fibers to be fully accelerated upon emerging from the tapered portion 86. The flow cross section at C, should be less than 20%, and can be less than five percent of the cross section at A. In one implementation of the invention having a flow diameter of 1.5 mm at C, the distance A to B is at least one inch and A to C at least about 1.5 inches, with a flow area reduction of about 80 per cent from A to C. This corresponds to a convergence angle of less than five degrees from A to B.

The shape of the tube 82 in accordance with the foregoing general parameters, is believed to cause the fibers 104, which are at best only mildly oriented at A, to reorient gradually as they accelerate through the tube, until each is oriented essentially on the tube axis as the fiber reaches region C. The gradual orientation of the fibers is represented by the particular fibers 104,106,108 and 110. Thus, although some fiber lengths may be greater than the diameter of the tube at and downstream of point B, the fibers have, between points A and B, become sufficiently axially oriented to virtually eliminate plugging as a problem during the analysis of a typical refiner output sample. Moreover, even if a typical shive, such as depicted at 112, should be present in the sample, it will have oriented itself sufficiently to avoid plugging. Very large shives (2-3 mm in width) should be filtered out before the size measurement begins.

With particular reference to FIG. 3, the fiber detection feature of the present invention will be described in greater detail. The notch 92 in housing 76 preferably extends about 180° to provide a convenient cradle into which optical detector 26 is secured, as by small screws 116 passing through flanged portion 118 of the detector into the housing 76. The detector device 26 includes a light source for illuminating the cylindrical wall portion 88 of the tube as the fluid passes therethrough and sensor means for detecting the variations in the intensity of the light that passes through the cylindrical wall portion in response to the passage of each dispersed fiber as the fluid passes therethrough. Preferably, the detector 26 is a slotted optical switch which projects an infrared beam from a gallium arsinide LED situated in lobe 116, for receipt at a sensor situated in lobe 118, whereby an analog output signal can be amplified and processed in a manner to be described below.

The light beam 122 is depicted in FIGS. 4 and 5. In the preferred embodiment, where the diameter at C, the measurement portion 88 of tube 82, is about 1.5 mm, the beam width shown in FIG. 4 is preferably no greater than 0.25 mm. The beam width can be greater than the desired fiber length measurement interval, but should be less than the smallest fiber length for which very accurate measurements are desired. In general, the beam height shown in FIG. 5, is at least equal to the tube diameter at the measurement portion 88. Thus, in the preferred embodiment, the optical device 26 projects a light beam which has a width dimension parallel to the axis, that is less than the inner diameter of the measurement portion of the tube, and a height dimension perpendicular to the axis and to the beam direction, that is greater than the diameter of the tube. Generally, the beam resembles a rectangular slab or ribbon spanning the gap between lobes 120 and 122.

The cell housing 76 as shown in FIG. 3, preferably has a connector plate 126 secured thereto, whereby the electrical leads 128 from the detector 26 may be connected to respective leads 130 by which the sensor signals are electronically, and preferably digitally, processed.

Figure 6:
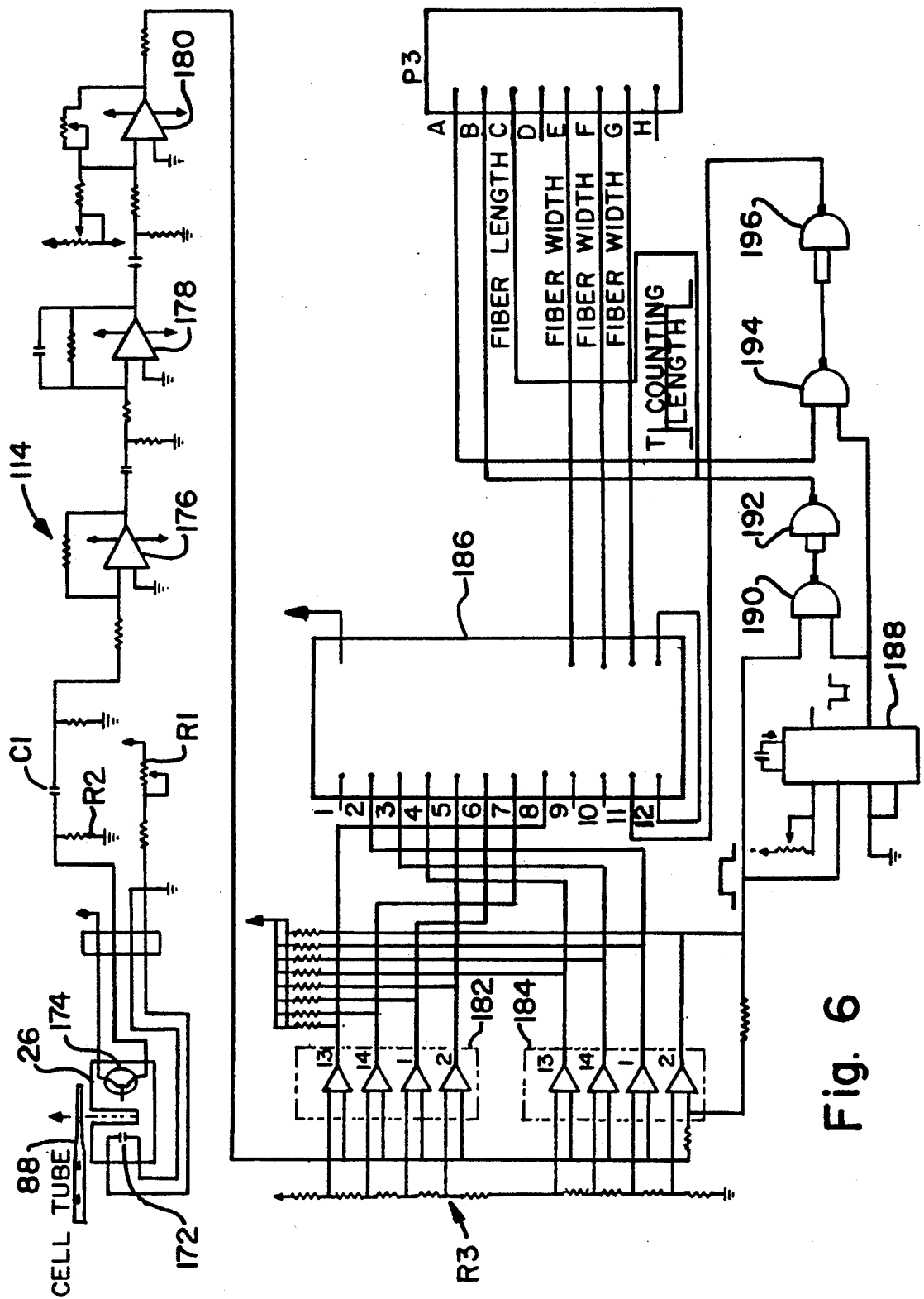
FIG. 6 is a circuit schematic for the preferred signal processing associated with the cell shown in FIG. 3.

FIG. 6 is a schematic of the preferred form of signal processing 114. The tube measurement portion 88 in which the fibers are traveling forms part of the detector, indicated generally at 26, which includes a light emitting diode 172 and a phototransistor or photodiode 174. As the fibers move in single file through the transparent tube, which is interposed between the LED 172 and the photodetector 174, the amount of light which is seen by the photodetector 174, will be a function of the length and width of each fiber. Thus, presuming that the rate of motion of the fibers is constant, the period of time the light received by the photodetector is below a nominal value commensurate with no interruption of the light path between the LED and photodetector, will be a function of the length of the fiber. The amount by which the light seen by the photodetector 174 is reduced will be a function of the diameter of the fiber. Thus, photodetector 174 will provide output pulses having a length and magnitude which are respectively commensurate with the length and diameter of a fiber which passes through the optical path between LED 172 and photodetector 174. The intensity of the light produced by LED 172 may be controlled via a variable resistance R1 which is connected in series with LED 172 between a current source and ground potential.

The photodetector 174 is connected as an emitter follower and the output pulses thus produced will appear across resistor R2. These output pulses are capacitively coupled, via a first coupling capacitor C1, to a first input terminal of a first of three series connected linear operational amplifiers 176. The amplified phototransistor output signal provided by amplifier 176 is delivered as an input to the second series connected operational amplifier 178. Amplifier 178, by virtue of its feedback circuit, further amplifies and shapes the pulses commensurate with fiber dimensions. The output of amplifier 178 is, in turn, delivered as an input to the third operational amplifier 180 which, again because of its feedback circuit, provides additional gain as well as offset control to reduce the noise below cutoff. The three amplification stages more easily provides high gain relative to the use of a single amplifier.

The information-containing pulses which appear at the output of amplifier 180 are delivered as inputs to a pair of low offset voltage quad comparators 182 and 184. As indicated schematically in FIG. 6, each of comparators 182 and 184 comprises four linear comparator amplifiers. The information-containing pulses are applied, in parallel, to the positive polarity input terminals of all eight comparators. A different reference voltage or logic level, derived from a voltage divider indicated generally at R3, is applied to the negative polarity input of each of the comparator amplifiers. The number of comparator amplifiers which are biased into conduction by the information containing pulse will, accordingly, be an indication of the magnitude of that pulse.

The eight outputs of the comparators 182 and 184 are delivered as separate inputs to an integrated circuit 186. In one reduction to practice of the invention, circuit 186 consists of a fuse programmable logic circuit configured to generate a three-bit digital signal commensurate with the state of the eight comparator output signals. This three-bit signal is indicative of fiber width. As will be appreciate by those skilled in the art, more than two of the quadcomparators could be employed if a higher degree of accuracy is desired. The output of IC 186 is delivered to a digital computer, not shown, for further processing.

The information containing pulses appearing the output of amplifier 180 are also provided to an input of a monostable multivibrator 188. Multivibrator 188 will provide, at its Q output terminal, a gating pulse having a preselected duration. This gating pulse, and the information-containing pulse, are applied to the inputs of a first NAND gate 190. The output of gate 190 is connected to both inputs of a further NAND gate 192. Gates 190 and 192 cooperate to define a filter to eliminate the effects of tiny specks which have little importance in fiber analysis. The output of gate 192 will be a "counting length" pulse, i.e., a pulse having a preselected magnitude and a width which is commensurate with the length of time the light received by photodetector 174 is reduced by the passage of a fiber through the tube. Thus, the output of gate 192 will be a direct measure of fiber length.

The output of multivibrator 188 is also provided as an input to a further NAND gate 194. The second input to gate 194 is provided as a reset pulse from the computer to reset the width-related IC 186. The output of NAND gate 194 is delivered to both inputs of a further NAND gate 196 and the output of gate 196 is connected to the reset input of IC 186.

Under the preferred conditions, e.g., concentrations of less than about 0.001 per cent fiber flowing at a velocity of about 160 feet per second through a tube measurement portion having a diameter of 1.5 mm, in excess of 12,000 fiber length and width measurements can be made in a one-minute run.

Thus, the sensor means 26,114 is preferably responsive to both the duration and magnitude of the variation in the intensity of detected light resulting from the passage of each fiber through the light beam. Significantly, both fiber length and fiber width can accurately be analyzed using a single light beam. Although the embodiment described herein utilizes an infrared LED, the invention can also be implemented using other forms of light, for example coherent, i.e., laser beam.

Referring again to FIG. 3, it should be appreciated that flow tube 82, which is preferably clear, rigid material such as blown glass, is supported coaxially within housing 76, at least at two locations, e.g., annular support 94 and annular support 96. These support members 94,96 are preferably permanently attached to the interior walls of housing 76 to provide apertures of different size for receiving and supporting tube 82.

Support 94 defines a relatively large aperture, for receiving and retaining the large diameter portion of tube 84, preferably at a circumferential recess or detent which thereby assures proper longitudinal registry of the tube 82 within the housing 76. It may be appreciated that, generally, the inlet end 84 of tube 82 is very nearly the same diameter as the diameter of inlet conduit 20, so that a simple overlapping of the preferably plastic or rubber tube onto end 84 provides sufficient sealing therebetween. Optionally, resilient conduit 20 may bear against the inside wall 94′ of the end 84 of housing 76, for providing equivalent support without a distinct structure 94.

On the other hand, support member 96 also serves a sealing function because the diameter at the second or outlet end 90 of the tube 82 may be much smaller than the diameter of the discharge conduit 24. Preferably, discharge conduit 24 and member 96 are permanently bonded to the discharge end 80 of the housing 76. A guide member 95 is preferably permanently situated within the housing 76 immediately adjacent the optical detector 26, and provides a tapered bore for guiding the leading end 90 of flow tube 82 through the detector 26 and into engagement with the member 96, which is also adjacent the detector 26.

Due to the low cost of the tube 82 used in the illustrated embodiment, it is considered disposable. This eliminates the need for difficult and time-consuming cleaning of the tube 82 when it becomes plugged or dirty. The tube 82 is simply removed and thrown away and a new tube 82 is fitted into place in the housing 76.

Figure 8:
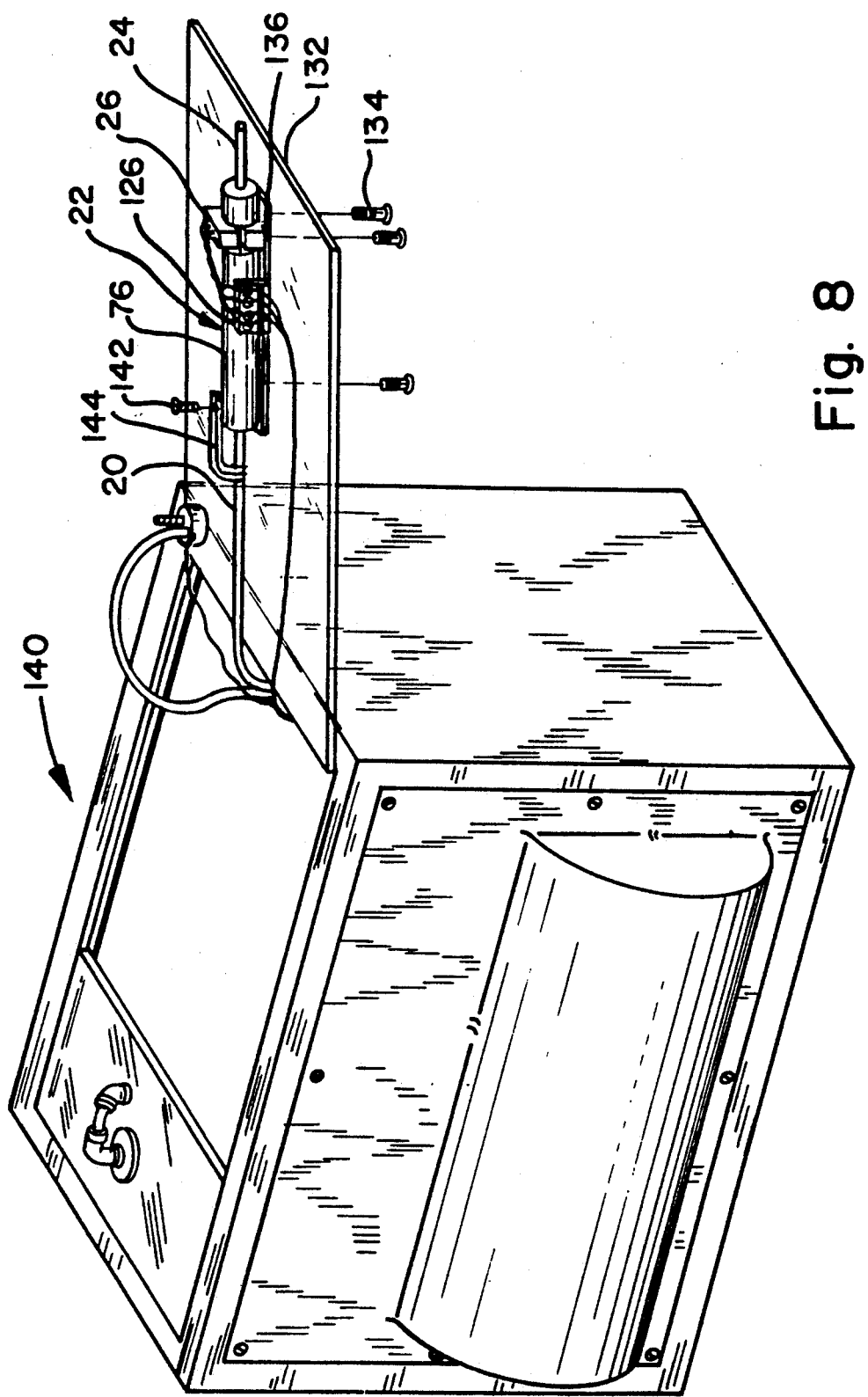
FIG. 8 is a detailed view of the hinged wall of the package of FIG. 7, open to expose the measuring cell for servicing.

The tube 82 is removed by first lifting the cell access lid 132 in the top of the instrument package 140, as shown in FIGS. 3, 7 and 8. Preferably, the housing 76 is attached to the access lid 132 by means of a fixture 136 and associated screws 134. The screw 142 holding the retaining bracket 144 for inlet conduit 20 to the cell housing 76, is removed. With a slight twisting motion, the tube 82 is pulled out of the housing 76. The old tube 82 is removed from the inlet hose 20 and a new tube is connected to hose 20. The lead end 90 of the new tube is carefully inserted into the housing 76, using a slight twisting motion to insert the fine end 90 of the tube 82 into the aperture at support member 96 near the return hose 24. The retaining bracket 144 is replaced. The access lid 132 is then returned while being sure that the return hose 24 is fed into the tank or drain. The fiber length analyzer is now ready for continued operation. In particular, it may be seen in FIGS. 7 and 8 that any of the walls of the analyzer box may be formed as a hinged door to which the detector cell 22 is attached.

It should be appreciated that, although the preferred embodiment of the invention is intended for analyzing the size distribution of fibers in a dilute concentration of less than about 0.001 weight percent in water, the invention in the preferred form described above, can advantageously be used to assess the particulate content of a very dilute concentration of particles disbursed in an otherwise substantially pure liquid, at concentrations on the order of 10 ppm. Moreover, once the carrier liquid, such as water, has been filtered and purified so as to provide a substantially uniform output from the processing circuitry 114 (FIG. 6), the introduction of particulates or chemical substances, such as glucose, can be detected. Each glucose molecule generates a corresponding, identifiable pulse in the circuitry 114.

Although particulates of this size, i.e., less than about 0.01 mm, cannot be classified as to length and width, the ability to detect the presence of "foreign" particulates at such low concentrations, and to obtain an output pulse for each such microscopic or submicroscopic particulate, is of major importance in fields such as environmental monitoring, medicine, and clean room operations. This high sensitivity is not necessarily dependent on assuring axial alignment of the particulates through the measurement portion of the tube, as is the case with fibers, so that the gradual transition in the flow tube is not believed critical in the particulate analyzer embodiment of the invention. Similarly, the portion 182, 184, and 186 of the circuitry of FIG. 6, which is specially adapted to classify fibers by width, is not required for general low concentration particle counting. Moreover, pulse duration, which is indicative of fiber length as determined at 188, 190, 192, 194, and 196, is not important, as long as a discernible, individual pulse is obtained from the passage of each particulate through the light beam. The important aspect of this high sensitivity, is the use of multiple, e.g., three high grain operational amplifiers 176, 178, and 180 (such as Type 741) for enhancing the sensor signal relative to noise.

It should also be appreciated that when measuring microscopic and submicroscopic particulates, the measuring tube diameter can be provided at the low end of the specified range, i.e., about 1.0 mm, without substantial risk of plugging, since particulates having a dimension on the order of 1.0 mm should not be present in the particulate sample. On the other hand, the upper end of the indicated range of measurement tube portion diameter, 3.0 mm, would accommodate most shives encountered in practical refiner applications. With the preferred diameter of 1.5 mm, typical shives are accommodated, but if the tube does plug, the ease with which the measuring tube can be cleaned and replaced, does not delay significantly, the data acquisition.

I claim:

1. A system for analyzing the size distribution of a wood pulp fiber sample comprising:
    (a) source means for providing a fluid consisting essentially of the wood pulp fiber sample dispersed in a liquid;
    (b) a measurement station including a measurement cell having an inlet and an outlet for said fluid and means for measuring the size of each fiber that passes through the cell from the inlet to the outlet;
    (c) first conduit means for delivering said fluid from the source means to the inlet of the measuring cell;
    (d) means for maintaining a substantially constant volumetric flow rate of fluid through the first conduit and measuring cell;
    (e) wherein the measurement cell includes
        (1) a single flow tube having a first end fluidly connected at the cell inlet only to the first conduit means, a second end fluidly connected to the cell outlet, and an axis between the first and second ends, said flow tube further having a substantially transparent measurement portion with a substantially round flow area having a diameter in the range of about 1.0–3.0 mm intermediate the ends and a transition portion that gradually narrows in the direction of flow between the first end and the measurement portion, such that the fibers accelerate in forward velocity through the transition portion and pass through the measurement portion on the tube axis in spaced-apart, serial order,
        (2) a light source for projecting a single beam of light at a preestablished intensity through the measurement portion transversely to the tube axis, as the fluid passes therethrough,
        (3) sensor means for detecting variations in the intensity of the light that passes through the measurement portion in response to the passage of each dispersed fiber through the beam as the fluid passes through the measurement portion; and
    (f) wherein the measurement station includes processing means responsive to the sensor means for recording fiber size distribution values commensurate with the variations in detected light intensity.

2. The system of claim 1, wherein the cross sectional flow area of the tube reduces in the transitional portion by at least about 75 per cent relative to the flow area at the first end.

3. The system of claim 2, wherein the inner diameter of the measurement portion is between about 1.5 and 2.5 mm and the source means is fluidly connected to a pulp refiner.

4. The system of claim 1, wherein the inner diameter of the measurement portion is between about 1.5 and 2.5 mm, said means for maintaining a constant flow rate maintains a rate in the range of 150–200 ft/sec, and the means for recording fiber distribution values records values of fiber length up to about 7.2 mm.

5. The system of claim 1, wherein the source means provides a fluid dispersion in which the fibers have a volume per cent concentration in water, of less than about 0.001 per cent.

6. The system of claim 1, wherein the gradual narrowing of the transition portion is at an angle of convergence of less than about 30° with the tube axis.

7. The system of claim 6, wherein
    the measuring cell includes a substantially tubular housing having first and second ends, a longitudinal axis, and a cut out transverse to the housing axis and intermediate the ends;
    said flow tube is situated coaxially in the housing such that the tube first end is adjacent the housing first end and the tube second end is adjacent the housing second end, with said measurement portion of the tube situated in radial registry with said cut out;
    said light source is supported at said cut out so as to project a ribbon beam of light through the measurement portion of the tube from only one side of and perpendicular to the tube axis; and
    said sensor means is situated at the cut out on the other side of the tube axis for directly receiving said beam.

8. The system of claim 7, wherein the light beam has a width dimension parallel to said axis, that is less than the inner diameter of the measurement portion, and a height dimension perpendicular to the axis and to the beam direction, that is greater than said inner diameter.

9. The system of claim 8, wherein the light beam width is no greater than about 0.25 mm.

10. The system of claim 7 wherein the sensor means is a single sensor responsive to the duration and magnitude of the variation in the intensity of detected light resulting from the passage of each fiber through said light beam.

11. The system of claim 7, wherein the housing includes means for removably supporting the flow tube within the housing.

12. The system of claim 11, wherein the first end of the flow tube is connected directly and removably on the first conduit and the second end of the flow tube is removably connected to seal means within the second end of the housing.

13. The system of claim 1, wherein
the measuring cell includes a substantially tubular housing having first and second ends, a longitudinal axis, and a cut out intermediate the ends and transverse to the housing axis;
said flow tube is situated coaxially in the housing such that the tube first end is adjacent the housing first end and the tube second end is adjacent the housing second end, with said measurement portion of the tube situated in radial registry with said cut out;
said light source is supported by the housing at the cut out so as to project a ribbon beam of light through the measurement portion of the tube from only one side of and perpendicular to the tube axis; and
said sensor means is a single sensor supported by the housing at the cut out on the other side of the tube axis.

14. A system for analyzing the size distribution of a wood pulp fiber sample comprising:
(a) source means for providing a fluid consisting essentially of the wood pulp fiber sample dispersed in a liquid;
(b) a measurement station including a measurement cell having an inlet and an outlet for said fluid and means for measuring the size of each fiber that passes through the cell from the inlet to the outlet;
(c) first conduit means for delivering only said fluid from the source means to the inlet of the measuring cells;
(d) means for maintaining a substantially constant volumetric flow rate of fluid through the first conduit and measuring cell;
(e) wherein the measurement cell includes
(1) a single flow tube fluidly connected at a first end only to the first conduit means and at a second end to the cell outlet, said flow tube having an axis, a substantially transparent measurement portion intermediate the ends and a transition portion that gradually narrows at an angle of convergence of less than about 30° to the axis in the direction of flow between the first end and the measurement portion, such that the fibers pass through the measurement portion aligned with the tube axis in spaced-apart, serial order,
(2) a single light source for projecting a single beam of light at a preselected intensity through the measurement portion transversely to the tube axis, as the fluid passes therethrough,
(3) single sensor means for detecting variations in the intensity of the light that passes through the measurement portion in response to the passage of each dispersed fiber through the beam as the fluid passes through the measurement portion; and
(f) wherein the measurement station includes processing means responsive to the sensor means for recording fiber size distribution values commensurate with the variation in detected light intensity.

15. The system of claim 14, wherein the cross sectional flow area in the measurement portion is between about 15 and 25 per cent of the flow area at the tube inlet.

16. The system of claim 14, wherein the tube diameter at the measurement portion is between about 1.0 and 3.0 mm.

17. The system of claim 16, wherein the transition portion extends at least about one inch in the axial direction and the measurement portion is situated at least about one-half inch downstream of the transition portion.

18. The system of claim 17, wherein the transition portion diameter is about 1.5 mm.

19. The system of claim 16, wherein said angle of convergence is less than about 15°.

20. A system for analyzing the size distribution of a fiber sample comprising:
(a) source means for providing a fluid consisting essentially of the fiber sample dispersed in a liquid;
(b) a measurement station including a measurement cell having an inlet and an outlet for said fluid and means for measuring the size of each fiber that passes through the cell from the inlet to the outlet;
(c) first conduit means for continuously maintaining a flow of said fluid from the source means to the inlet of the measuring cell;
(d) second conduit means for continuously maintaining a discharge flow of said fluid out from the outlet of the measuring cell;
(e) means for maintaining a substantially constant volumetric flow rate of fluid through the first conduit, measuring cell, and second conduit;
(f) wherein the measurement cell includes
(1) a hollow, elongated housing defining a flow axis,
(2) a flow tube coaxially and removably supported within the housing and fluidly connected at a first end to the first conduit and at a second end to the second conduit, said flow tube having a substantially transparent, measurement portion intermediate the ends, such that the fibers pass through the measurement portion on the tube axis in spaced-apart, serial order,
(3) a light source secured to the housing for projecting a single beam of light through the measurement portion transversely to the tube axis, as the fluid passes therethrough,
(4) sensor means secured to the housing for detecting variations in the intensity of the light that passes through the measurement portion in response to the passage of each dispersed fiber through the beam as the fluid passes through the measurement portion; and
(g) wherein the measurement station includes processing means responsive to the sensor means for recording fiber size distribution values commensurate with the variation in detected light intensity.

21. The system of claim 20, wherein
the housing is substantially tubular, has first and second ends, and a cutout intermediate the ends and transverse to the axis;

said flow tube is situated coaxially in the housing such that the tube first end is adjacent the housing first end and the tube second end is adjacent the housing second end, with said measurement portion of the tube situated in radial registry with said cut out;

said light source is supported by the housing at the cutout so as to project a ribbon beam of light through the measurement portion of the tube from only one side of and perpendicular to the axis; and said sensor means is supported by the housing at the cutout on the other side of the axis.

22. The system of claim 21, including means within the housing adjacent the light source, for removably receiving and supporting the second end of the tube coaxially in the housing.

23. The system of claim 20, wherein the system is enveloped by a console package having at least one movable wall, the measuring cell housing is attached to the movable wall, and the wall is selectively movable between a closed position in which the measuring cell is within the console and an open position in which the cell is outside the console, whereby the tube can be replaced in the housing without detaching the housing from the wall and without deteaching the light source and sensor means from the housing.

24. A system for analyzing the particulate content of a fluid sample comprising:

(a) source means for providing a fluid consisting essentially of said particulates dispersed in an otherwise substantially pure liquid at a concentration of less than about 0.001 per cent, (b) a measurement station including a measurement cell having an inlet and an outlet for said fluid and means for sensing each particle that passes through the cell from the inlet to the outlet;

(c) first conduit means for continuously maintaining a flow of said fluid from the source means to the inlet of the measuring cell;

(d) second conduit means for continuously maintaining a discharge flow of said fluid out from the outlet of the measuring cell;

(e) means for maintaining a substantially constant volumetric flow rate of fluid through the first conduit, measuring cell, and second conduit;

(f) wherein the measurement cell includes (1) a flow tube fluidly connected at a first end only to the first conduit means and at a second end to the second conduit means, said flow tube having an axis and a tapered angle of convergence of less than about 30° preceding a substantially transparent measurement portion with a round flow diameter in the range of about 1.0–3.0 mm such that the particles pass through the measurement portion in spaced-apart, serial order;

(2) a slotted optical switch light source for projecting a single beam of light through the measurement portion transversely to the tube axis, as the fluid passes therethrough;

(3) sensor means for detecting, without polarization or beam splitting, variations in the intensity of the light that passes through the measurement portion in response to the passage of each dispersed particle through the beam as the fluid passes through the measurement portion and for generating a sensor signal commensurate with said intensity; and (g) wherein the measurement station includes processing means including a cascaded series of high gain operational amplifiers, responsive to the sensor signal, for counting particles commensurate with the variation in detected light intensity.

* * * * *